(12) United States Patent
Hillman

(10) Patent No.: US 9,746,263 B2
(45) Date of Patent: Aug. 29, 2017

(54) LEFT SIDE CHARGING HANDLE FOR A RIFLE

(71) Applicant: Camaron Randolph Hillman, Vestal, NY (US)

(72) Inventor: Camaron Randolph Hillman, Vestal, NY (US)

( * ) Notice: Subject to any disclaimer, the term of this patent is extended or adjusted under 35 U.S.C. 154(b) by 2 days.

(21) Appl. No.: 14/450,336

(22) Filed: Aug. 4, 2014

(65) Prior Publication Data
US 2014/0345444 A1 Nov. 27, 2014

Related U.S. Application Data

(60) Provisional application No. 61/862,353, filed on Aug. 5, 2013.

(51) Int. Cl.
| | |
|---|---|
| *F41A 7/02* | (2006.01) |
| *F41A 3/72* | (2006.01) |
| *F41A 35/06* | (2006.01) |
| *G01N 15/06* | (2006.01) |
| *G01N 21/84* | (2006.01) |

(52) U.S. Cl.
CPC ........ *F41A 3/72* (2013.01); *F41A 7/02* (2013.01); *F41A 35/06* (2013.01); *G01N 15/06* (2013.01); *G01N 21/84* (2013.01)

(58) Field of Classification Search
CPC ...... F41A 7/00; F41A 7/02; F41A 3/72; F41A 35/06
USPC ............................. 89/1.4, 1.42; 42/16, 25, 72
See application file for complete search history.

(56) References Cited

U.S. PATENT DOCUMENTS

| | | | | |
|---|---|---|---|---|
| 6,019,024 A * | 2/2000 | Robinson | .................. | F41A 3/72 89/1.42 |
| 7,231,861 B1 * | 6/2007 | Gauny | ...................... | F41A 3/72 42/16 |
| 8,567,301 B1 * | 10/2013 | Sharron | .................... | F41A 3/72 89/1.4 |
| 8,863,632 B1 * | 10/2014 | O'Malley | ................ | F41A 3/72 42/16 |
| 2010/0000396 A1 * | 1/2010 | Brown | ...................... | F41A 3/72 89/1.4 |
| 2011/0083551 A1 * | 4/2011 | Sirochman | ................ | F41A 3/72 89/191.01 |

(Continued)

*Primary Examiner* — Jonathan C Weber
(74) *Attorney, Agent, or Firm* — Eric B. Fugett; Mark A. Pitchford; Waller Lansden Dortch & Davis, LLP

(57) ABSTRACT

A Picatinny mounted, left side charging handle system adapted for mounting on AR-15, M-4, or M-16 and similar rifles. The charging handle mounts on the foremost Picatinny mount of the upper receiver and replaces OEM charging handles provided with the rifle. Side mounting overcomes the problem of a shooter's finger being moved from the trigger and/or the shooter's cheek moving from the stock weld so that the shooter's eyes may remain on the intended target. The novel charging handle mounts on the upper receiver and readily accommodates mounting virtually any optical device in addition to the charging handle. The novel charging handle may be mounted to the rifle with no rifle modification required. Rifles may alternately be charged by pulling back a protruding rear portion of the charging handle. The apparatus may readily be transferred between rifles. The rifle equipped with novel charging handle remains fully field strippable without tools.

18 Claims, 6 Drawing Sheets

(56) References Cited

U.S. PATENT DOCUMENTS

2011/0271827 A1* 11/2011 Larson ............... F41A 5/28
  89/193
2014/0068988 A1* 3/2014 Donahue ............. F41A 3/72
  42/69.01

* cited by examiner

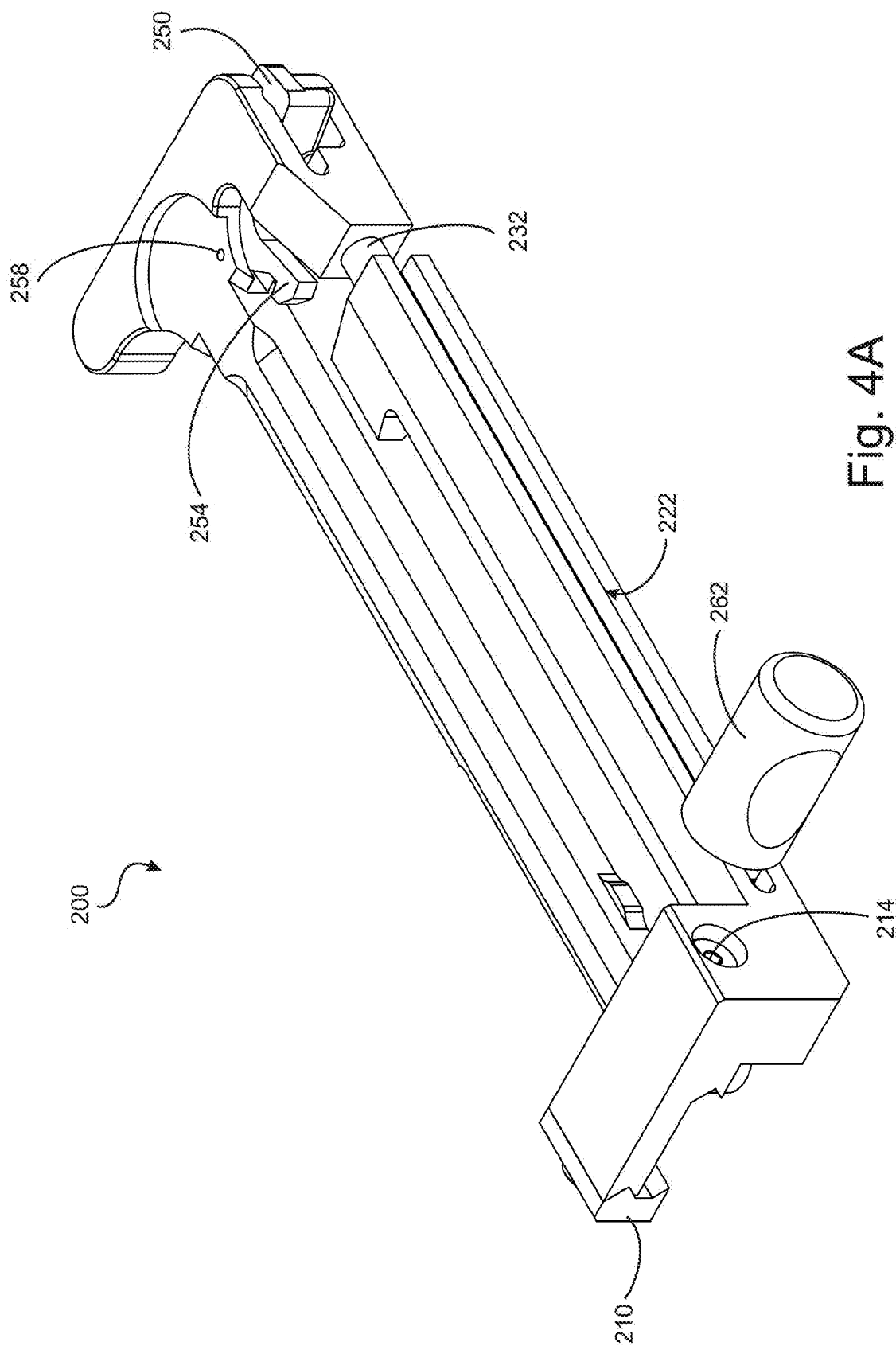

LEFT SIDE CHARGING HANDLE FOR A RIFLE

RELATED APPLICATIONS

This application claims priority in accordance with 37 C.F.R. §1.19(e) to U.S. Provisional Patent Application Ser. No. 61/862,353 filed Aug. 5, 2013 for AR-15 PICATINNY MOUNTED LEFT SIDE MOUNTED CHARGING HANDLE which is included incorporated herein in its entirety by reference.

FIELD OF THE INVENTION

The invention pertains to charging handles for firearms and, more particularly, to a Picatinny mounted, left side mounted charging handle for an AR-15, M-4, and M-16 rifle platforms.

BACKGROUND OF THE INVENTION

Charging handles or cocking handles or bolt handles for rifles are well known and universally used to perform several functions related to loading, cocking, firing, and ejecting shells in cooperation with a rifle. The charging handle, when operated, causes the rifle's hammer or striker to be cocked (i.e., moved to the ready position) thereby allowing the operator of the rifle (i.e., the shooter) to pull the bolt rearward. This action facilitates several possible actions. For example, this action may eject a spent shell casing or unfired cartridge from the rifle's chamber.

Another action typically accomplished by the bolt's rearward motion is loading a round of ammunition from a magazine or a hand-inserted single round.

Clearing a stoppage caused by a jam, a double feed, a stovepipe or a misfire is yet another action accomplished by the rearward motion of the bolt.

The rearward bolt movement verifies that the weapon's chamber is clear of any rounds or other obstructions.

Finally, the rearward motion of the bolt may release a bolt locked to the rear. This situation may occur after the last round on a firearm equipped with a last-round-hold-open feature has been fired.

Charging handles may vary significantly between rifle models. Several common forms of charging handle range from small protrusions or hooks from the side of the bolt to a pumped slide or lever.

The AR-15 rifle is a lightweight, 5.56 mm/0.223-caliber, magazine-fed, air cooled rifle with a rotating-lock bolt, typically actuated either by a direct impingement gas mechanism or alternately by a long/short stroke piston operation. The AR-15 rifles were first built by ArmaLite as a small arm rifle for the United States armed forces. ArmaLite sold the AR-15 design to Colt (i.e., Colt's Manufacturing Company LLC) who modified the rifle by relocating the charging handle from under the carrying handle (like the AR-15s predecessor the AR-10) to the rear of the receiver. Colt trademarked the name AR-15®. This redesigned rifle was subsequently adopted as the M16 rifle. The M-16® subsequently became available in semi-automatic versions. Since the early 1960s, the term AR-15® has applied only to semi-automatic versions of the rifle. While the name "AR-15" remains a Colt registered trademark, as is widely known to those of skill in the firearms arts, variants of the firearm are still independently made, modified and sold under various names by multiple manufacturers.

Charging handles of the prior art suffer from several deficiencies. For example, when a shooter is in a high stress circumstance such as being under fire, fine motor skills tend to diminish. Also, when in a firefight, receiving a gunshot wound to the hand is not uncommon. Diminished small motor skills for whatever reason may result in difficulty grabbing latches on prior art charging handles.

Many charging handles of the prior art are adaptable to the AR-15®. M-4® and M-16® rifles have been mounted in positions that limit the efficiency of a shooter. These awkward mounting arrangements often force the shooter to move his or her support hand a long distance to, for example, a rear positioned charging handle. When moving the support hand is required, the shooter typically loses significant control of the rifle.

Another consequence arising from prior art charging handles is that a shooter may be required to move his or her finger from the trigger to operate the charging handle.

Further, the shooter sometimes must move his or her cheek from the stock weld, thereby causing the shooter's eyes to be drawn away from the sight or "scope".

It would, therefore, be advantageous to provide a charging handle that overcomes these and other disadvantages of charging handles of the prior art.

SUMMARY OF THE INVENTION

In accordance with the present invention there is provided a Picatinny mounted, left side charging handle system adapted for mounting on AR-15®, M-4®, M-16® and other similar platforms. The novel charging handle mounts on the foremost Picatinny mount of the flat top upper receiver and replaces OEM charging handles provided with the rifle. The shooter's efficiency (e.g., speed, accuracy) is enhanced by the smaller amount of movement of the support hand, shooting hand, and/or face required to charge the rifle.

Side mounting overcomes the problem of a shooter's finger being moved from the trigger and/or the shooter's cheek moving from the stock weld so that the shooter's eyes may remain on the intended target.

A dual action charging is provided that allows ambidextrous operation of the novel charging handle. Normally, charging is effected using the side mounted handle. If the shooter is unable to readily charge his or her rifle, he or she may greatly endanger them self. The novel left-mounted charging handle of the invention allows charging the rifle with a body part (e.g., forearm, leg, etc.) other than the hand, or an external static object (e.g., belts, tables, door jambs, etc.). If the shooter is unable to use the side handle, a failsafe alternate charging mechanism is provided by the protruding portion of the release lever.

The novel charging handle mounts on the flat top upper receiver and readily accommodates mounting virtually any optical device in addition to the charging handle.

The novel charging handle may be mounted to the rifle with no rifle modification required. The apparatus may readily be transferred between rifles by loosening and subsequently re-tightening a single screw.

Operator and design errors are common with charging handles of the prior art. These errors are typically caused by such factors as torque on the charging handle, stress on the release lever tooth when the charging handle is pulled before disengaging, and stress on the release lever pin.

The novel charging handle allows the rifle to which it is attached to remain fully field strippable without tools. Typically, no tools are ever required for maintenance or take down of the charging handle in accordance with the invention.

BRIEF DESCRIPTION OF THE DRAWINGS

Various objects, features, and attendant advantages of the present invention will become more fully appreciated as the same becomes better understood when considered in conjunction with the accompanying drawings, in which like reference characters designate the same or similar parts throughout the several views, and wherein:

FIG. 4A is a top perspective, schematic view of the charging handle of FIG. 3 with all components assembled;

DETAILED DESCRIPTION OF THE PREFERRED EMBODIMENT

The present invention provides a Picatinny mounted, left side charging handle system adapted for mounting on the flat top AR-15®, M-4®, M-16® and other similar rifles.

Figure 1:
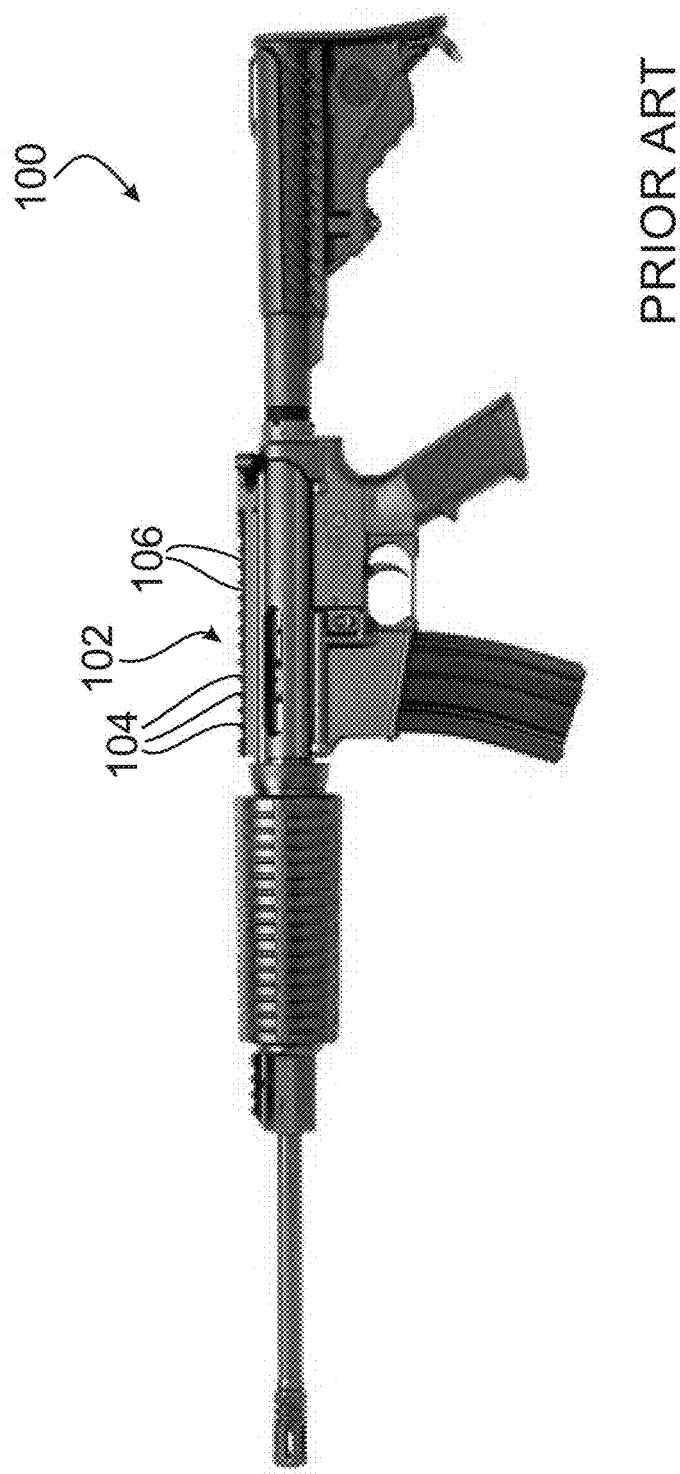
FIG. 1 is a side perspective, photographic, schematic view of a typical AR-15® rifle with a Picatinny rail mounted thereupon in accordance with the prior art.

Referring first to FIG. 1, there is shown a side perspective, photographic, schematic view of a typical AR-15® rifle 100 with a Picatinny rail 102 either built into or mounted thereupon. As used hereinafter, the term "AR-15", while recognizing the registered trademark of Colt, is used generically to refer to the AR-15® rifle and all other similar rifles.

The Picatinny rail 102 (also known as a MIL-STD-1913 rail, STANAG 2324 rail, or tactical rail), is a bracket attachable to the "AR-15" rifle that provides a standard mounting platform for accessories and attachments. The Picatinny rail 102 consists of an elongated T-section having a major axis. A series of ridges 104 interspersed with flat "spacing slots" 106 are disposed along the major axis. Accessories may be mounted to the Picatinny rail 102 in several manners. For example, the accessory, not shown, may be slid onto Picatinny rail 102 from one end or the other end. Another method for attaching an accessory to the "AR-15" uses a Weaver mount, not shown, that is clamped to Picatinny rail 102 with bolts, thumbscrews or levers. Weaver mounts are believed to be well known and, consequently, are not further discussed herein.

Figure 2A:
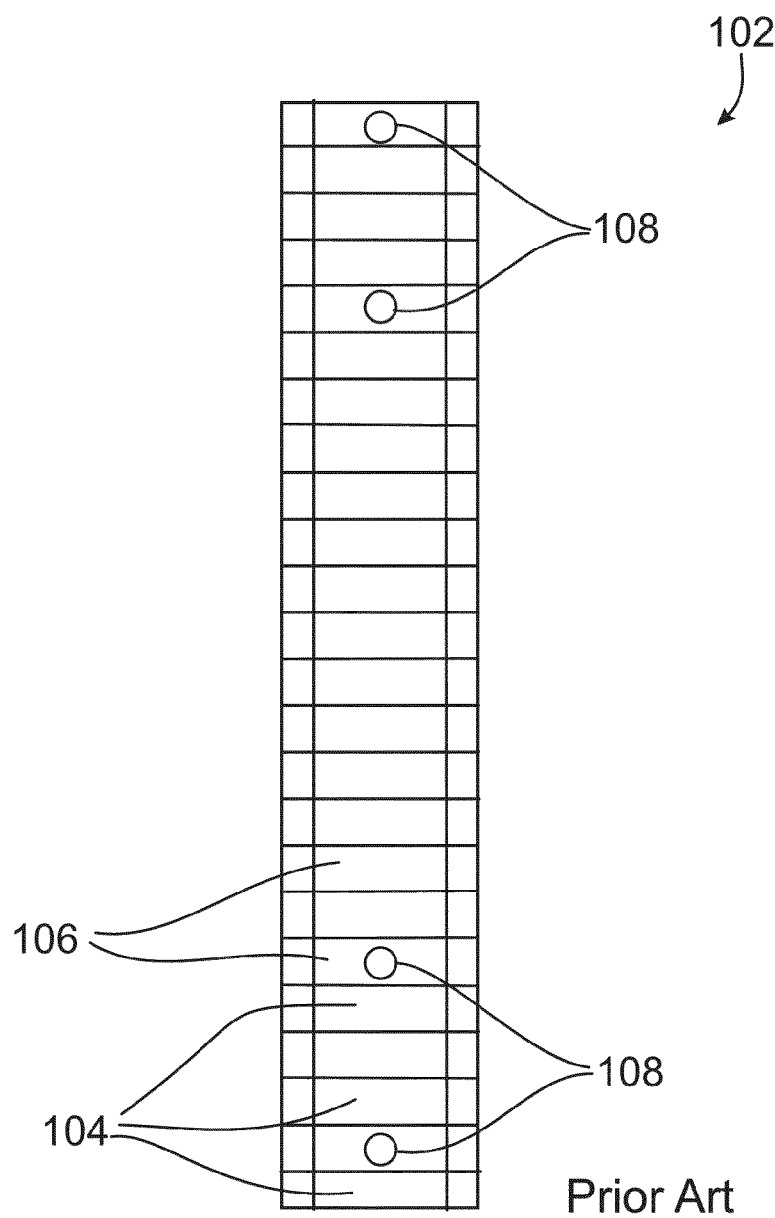
FIG. 2A is a top plan, schematic view of a typical Picatinny rail of the prior art.
Figure 2B:
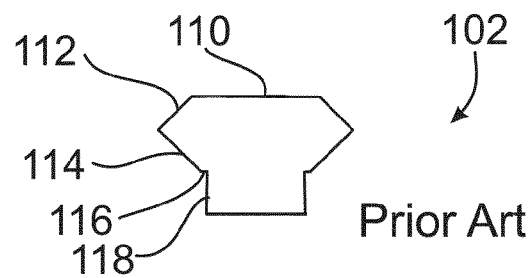
FIG. 2B is an end elevational, schematic view of the Picatinny rail of FIG. 2A.

Referring now also to FIGS. 2A and 2B, there are shown top plan and end elevational schematic views, respectively, of a typical Picatinny rail 102 showing more detail than Picatinny rail 102 mounted to an "AR-15" rifle as shown in FIG. 1.

Picatinny rail 102 has a sequence of raised ridges and slots, both disposed perpendicularly to a major axis, not specifically identified, of Picatinny rail 102. Raised ridges are shown at reference number 104 while intervening slots are shown at reference number 106.

Mounting holes 108 may be provided for securing Picatinny rail 102 to an external environmental object, for example an "AR-15" rifle.

FIG. 2B shows an end elevational cross section of Picatinny rail 102. The unique shape facilitates attaching and stabilizing any attached accessories. Stability is typically very important for rifle-mounted device, particularly when attaching sights and scopes.

Picatinny rail 102 has a flat upper surface 110 on top of raised ridges 104 and an upper sloping surface 112 adjacent a lower sloping surface 114. A short, indented horizontal surface 116 is disposed adjacent lower sloping surface 114 and abuts a vertical surface 118.

Figure 3:
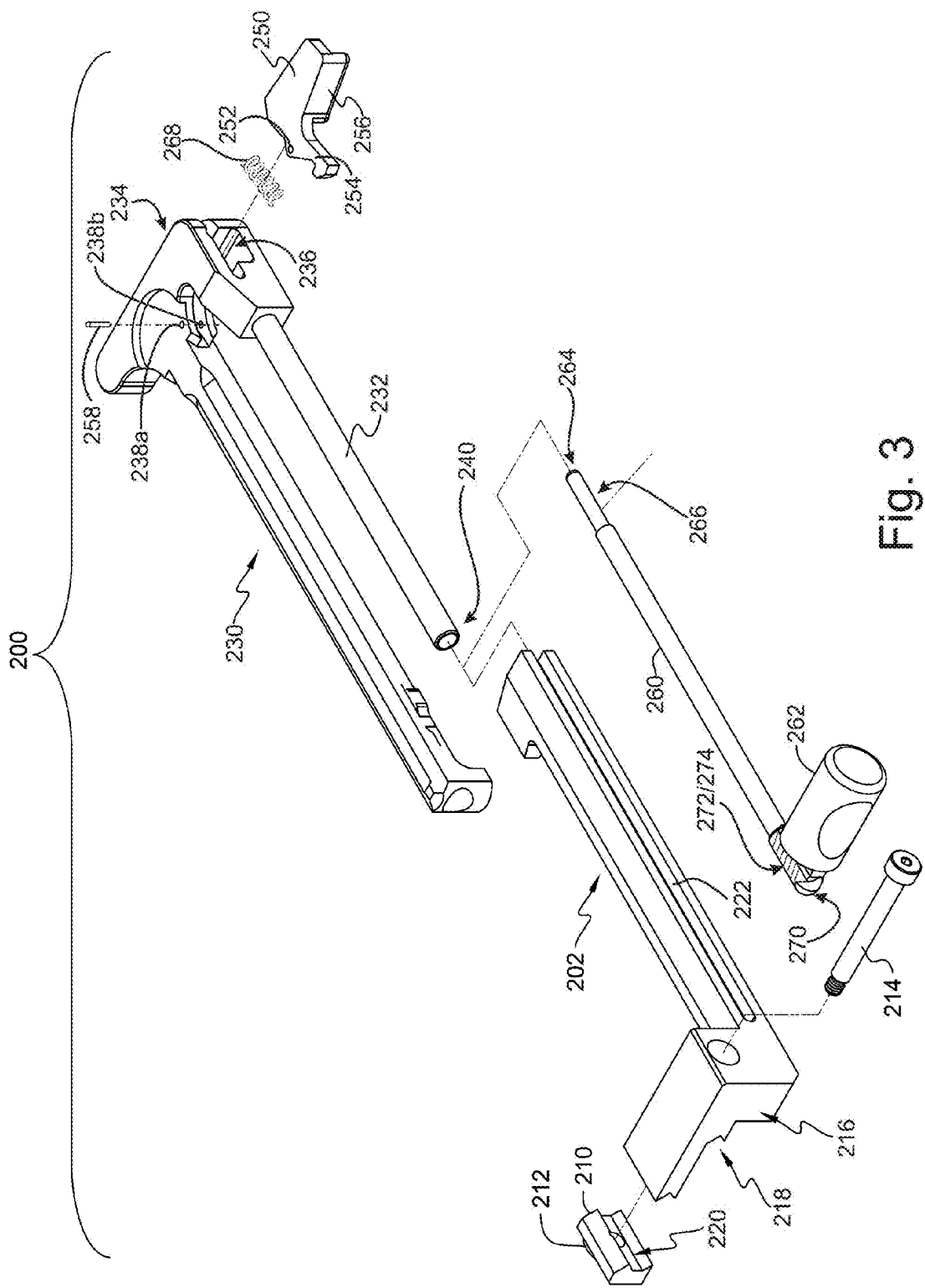
FIG. 3 is a side perspective, exploded, schematic view of the charging handle in accordance with the invention.

Referring now also to FIG. 3, there is shown a side perspective, exploded, schematic view of the charging handle in accordance with the invention, generally at reference number 200.

Charging handle 200 has a charging handle receiver 202 that forms the foundation of charging handle 200. Charging handle receiver 202 is mounted to the Picatinny rail 102 (FIGS. 2A and 2B) at its proximal end 216. A contour 218 at distal end 216 is adapted for engagement with regions 112 and 114 of Picatinny rail 102.

A similar contour 220 is provided on clamp 210. Picatinny rail 102 is gripped by contours 218, 210 as clamp 210 is tightened by clamp shoulder bolt 214 interacting with captive nut 212 retained in clamp 210. When clamp shoulder bolt 214 is tightened sufficiently, charging handle receiver 202 is retained on Picatinny rail 102.

Charging handle 230 attaches to charging handle receiver 202. An elongated hollow tube 232 projects forward from a rear portion 234 of charging handle 230. Elongated hollow tube 232 is received in a groove 222 in charging handle receiver 202.

Release lever 250 fits into an opening 236 in rear portion 234 of charging handle 230. Release lever 250 has a hole 252 through a hook portion 254 thereof. When release lever 250 is properly positioned in opening 236, hole 252 is aligned with upper hole 238a and lower hole 238b in rear portion 234 of charging handle 230. A release lever roll pin 258 is inserted through holes 238a, 252, and 238b and provides an axle on which release lever 250 may rotate in response to a force exerted on surface 256 as is discussed in detail hereinbelow.

Prior to insertion of release lever 250 into opening 236 during assembly, a release lever coil spring 268 is inserted into opening 236 so that release lever spring 268 is compressed by release lever 250 during rotation thereof.

A proximal end 264 of release lever rod 260 is inserted into distal end 240 of hollow elongated tube 232. Distal end 264 is sized and configured for interaction with surface 256 of release lever 250.

A handle assembly 262 is screwably affixed at a distal end 270 of release lever rod 260. External threads 272 on release lever rod 260 proximate distal end 270 are sized and configured to mate with internal threads 274 on handle assembly 262. Among other functions, release lever spring 268 exerts pressure on both release lever 250 and provides a restoring force to return handle 262 to its normal rest position upon completion of a charging operation. Charging operation is discussed in more detail hereinbelow.

Figure 4B:
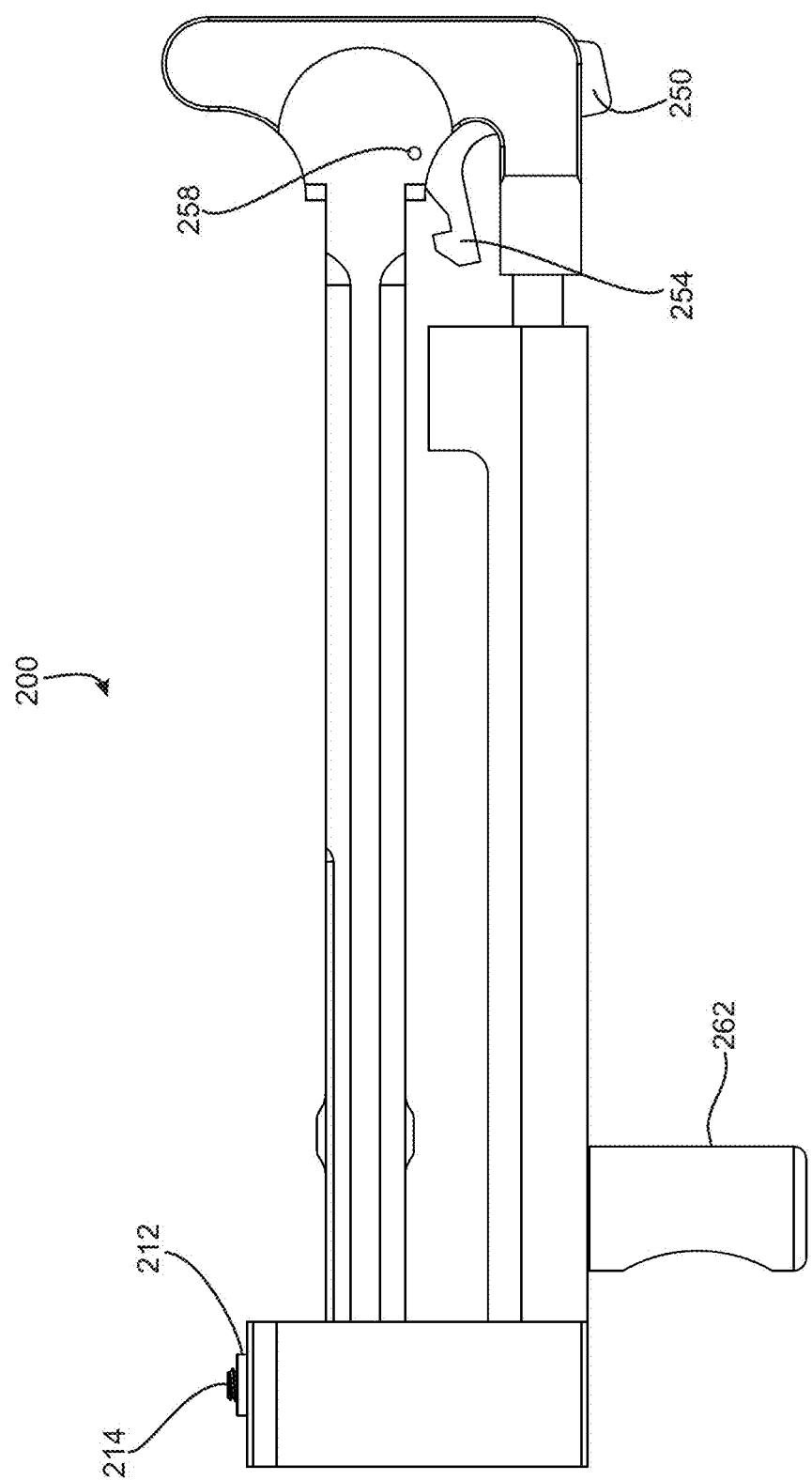
FIG. 4B is a top plan, schematic view of the charging handle of FIG. 3 with all components assembled.

Referring now also to FIGS. 4A and 4B, there are shown top perspective schematic and top plan schematic views, respectively, of the charging handle of FIG. 3 with all components assembled. While only a few of the components identified in FIG. 3 are shown in FIGS. 4A and 4B, key components are identified to clearly show how the novel left side mounted charging handle 200 of the invention is assembled.

Figure 5:
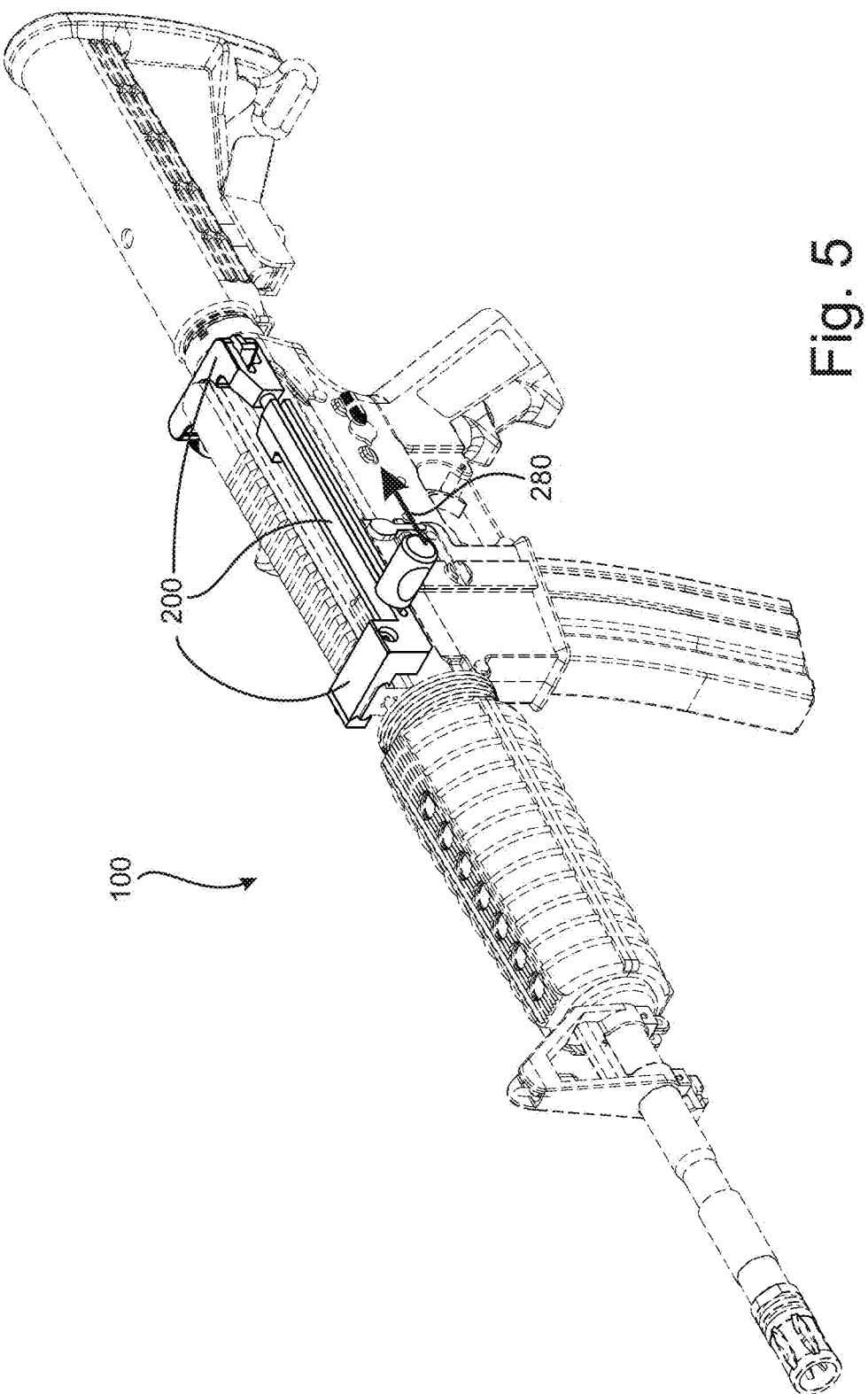
FIG. 5 is a top perspective, schematic view the rifle of FIG. 1 having the charging handle of FIGS. 3, 4A, and 4B installed thereupon.

Referring now also to FIG. 5, there is shown a "AR-15" rifle 100 similar to that shown in FIG. 1 but having the novel left side mounted charging handle 200 mounted thereupon.

In operation, after charging handle receiver 202 is mounted, typically on the foremost Picatinny mount of the rifle's upper receiver, the operator (i.e., shooter), attaches the pull handle 262 to release lever rod 260. The operator then inserts release lever rod 260 into groove 222, pull handle 262 first, on charging handle receiver 205.

The elongated hollow tube 232 is slid over release lever rod 260 and then charging handle 230 is rotated counter-clockwise into place in the rifle's upper receiver, not specifically identified and forming no part of the invention. By placing charging handle 260 into the upper receiver, the left side of the charging handle 230 aligns itself with charging handle receiver 202. However, before moving charging handle 230 completely forward, the operator must insert the bolt carrier group, not shown and forming no part of the invention, into the upper receiver. When the bolt carrier group is in place, the operator can then push the charging handle 230 all the way forward and then he or she can connect the upper receiver with the lower receiver, not specifically identified and forming no part of the invention.

The rifle 100 may now be charged (i.e., the bolt pulled back and a round placed into the chamber, none of which are specifically identified, nor do they form any part of the invention). This is accomplished by the operator pulling handle 262 back in the direction shown by arrow 280 (FIG. 5) until it stops and subsequently, releasing handle 262. The restoring force exerted by spring 268 moves handle 262 to its original, forward position.

When the operator pulls handle 262 backwards, that action pushes the release lever rod 260 into contact with surface 256 of release lever 250. Pressure on surface 256, causes release lever 250 to pivot release lever roll pin 258 and compress the release lever spring, 268. The rotation of release lever 250 disengages charging handle 230 from the rifle's upper receiver thereby allowing handle 262 to pull back freely thereby charging rifle 100. During this process charging handle receiver 202 guides charging handle 230 as it moves back and forth. The guiding provided by charging receiver 202 keeps charging handle 120 from shifting and causing torque from the charging handle 230 in the upper receiver. The charging handle receiver 202 is held in the front where it mounts to the Picatinny rail 102 and it also presses against the rifle's upper receiver at the back of the charging handle receiver. At this point, a rubberized backing, not shown, may be affixed charging handle receiver 202 to prevent marring of the upper receiver.

Another option for charging rifle 100 is to pull back a protruding portion of the release lever 150 with either hand until it stops, thereby charging rifle 100 in a manner similar to how the rifle would have been charged absent the presence of the left side charging handle in accordance with the invention.

Since other modifications and changes varied to fit particular operating requirements and environments will be apparent to those skilled in the art, the invention is not considered limited to the example chosen for purposes of disclosure, and covers all changes and modifications which do not constitute departures from the true spirit and scope of this invention.

Having thus described the invention, what is desired to be protected by Letters Patent is presented in the subsequently appended claims.

What is claimed is:

1. A left side charging handle system for a firearm, comprising:
   a) a charging handle receiver including an elongated body having a forward end, a rearward end, a body length extending from said forward end to said rear end, a left side, a right side opposite said left side, a top surface, a bottom surface opposite said top surface, a horizontal guide groove defined in said left side, and a selectively releasable clamping member adapted to securely mount said charging handle receiver to a mounting rail located on an upper surface of an upper receiver of said rifle;
   b) a charging handle including a forward shaft portion and a rear handle portion, the forward shaft portion extending forwardly from said rear handle portion, the rear handle portion having a left handle side, a right handle side opposite the left handle side, and a tubular structure protruding forwardly from said left handle side, said tubular structure slidably received in said groove;
   c) a release lever pivotally coupled to said left handle side, said release lever configured to engage an upper receiver of said firearm when said charging handle is in a rest position;
   d) a release lever rod slidably received in said tubular structure, said release lever rod having a forward rod end, a rearward rod end opposite the forward rod end, and a pull handle coupled to a portion of said release lever rod proximate to said forward rod end, said release lever rod configured to selectively disengage said release lever from said upper receiver and move said charging handle rearward to a charging position upon the application of rearward force to said pull handle when said charging handle receiver is mounted to said mounting rail.

2. The charging handle system of claim 1, wherein said clamping member extends from said top surface at an angle substantially transverse to said body length such that said body extends alongside a left side of said upper receiver when said charging handle receiver is mounted to said mounting rail.

3. The charging handle system of claim 1, wherein said clamping member extends from said top surface at an angle substantially transverse to said body length such that said body extends alongside said upper receiver below said upper surface of said upper receiver when said charging handle receiver is mounted to said mounting rail.

4. The charging handle system of claim 1, wherein said clamping member includes a cross member contoured to engage a side of said mounting rail, a clamp contoured to engage an opposite side of said mounting rail, a captive nut secured in said clamp, and a shoulder bolt extending through said cross member for selectively releasable engagement with said nut.

5. The charging handle system of claim 1, wherein said left handle side includes an opening defined therein, and said release lever is received in said opening.

6. The charging handle system of claim 5, wherein said release lever extends outwardly from said opening beyond an exterior surface of said left handle side.

7. The charging handle system of claim 5, further comprising a release lever spring received in said opening, said spring configured to bias a portion of said release lever toward said upper receiver.

8. The charging handle system of claim 5, wherein said tubular structure defines a passage extending through said tubular structure and a portion of said left handle side, said passage in fluid communication with said opening.

9. The charging handle system of claim 1, wherein said mounting rail is a Picatinny rail.

10. The charging handle system of claim 1, wherein said horizontal guide groove extends through said rearward end of said body but not said forward end of said body.

11. The charging handle system of claim 1, wherein an outer surface of said forward rod end comprises threads, and said pull handle comprises a threaded aperture configured to selectively engage said threads, whereby said pull handle may be selectively attached to and detached from said release lever rod.

12. The charging handle system of claim 1, wherein said release lever is pivotally coupled to said left handle side by a roll pin about which said release lever pivots.

13. The charging handle system of claim 1, wherein said firearm is an AR-type rifle or pistol.

14. The charging handle system of claim 1, wherein the application of rearward force to said pull handle causes said release lever rod to slide coaxially rearward through said tubular structure so that said rearward rod end contacts a surface of said release lever to disengage said release lever from said upper receiver.

15. The charging handle system of claim 1, wherein the application of rearward force to said pull handle causes said tubular structure to slide coaxially rearward through said guide groove and move said charging handle rearward to a charging position.

16. The charging handle system of claim 1, wherein said a portion of said pull handle is received in said groove.

17. The charging handle system of claim 16, wherein a portion of said pull handle extends outwardly from said groove.

18. The charging handle system of claim 1, wherein said charging handle receiver further includes a support portion extending from said right side at an angle substantially transverse to said body length, said support portion contacting a left side of said upper receiver to stabilize said charging handle system when said charging handle receiver is mounted to said mounting rail.

* * * * *

UNITED STATES PATENT AND TRADEMARK OFFICE
CERTIFICATE OF CORRECTION

PATENT NO. : 9,746,263 B2
APPLICATION NO. : 14/450336
DATED : August 29, 2017
INVENTOR(S) : Camaron Randolph Hillman It is certified that error appears in the above-identified patent and that said Letters Patent is hereby corrected as shown below:

In the Claims

At Column 6, Line 16, of Claim 1, delete the word "rifle" and replace it with the word --firearm--

Signed and Sealed this
Thirtieth Day of July, 2019

Andrei Iancu
*Director of the United States Patent and Trademark Office*